(12) United States Patent
Lee et al.

(10) Patent No.: US 11,040,324 B2
(45) Date of Patent: Jun. 22, 2021

(54) POLYELECTROLYTE MICROCAPSULES AND METHODS OF MAKING THE SAME

(71) Applicant: The Trustees Of The University Of Pennsylvania, Philadelphia, PA (US)

(72) Inventors: Daeyeon Lee, Wynnewood, PA (US); Junsang Doh, Seoul (KR); Miju Kim, Philadelphia, PA (US); Martin F. Haase, Philadelphia, PA (US); Gang Duan, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 15/097,874

(22) Filed: Apr. 13, 2016

(65) Prior Publication Data

US 2016/0332131 A1 Nov. 17, 2016

Related U.S. Application Data

(60) Provisional application No. 62/146,586, filed on Apr. 13, 2015.

(51) Int. Cl.
*B01J 13/06* (2006.01)
*A01N 25/28* (2006.01)
(Continued)

(52) U.S. Cl.
CPC .............. *B01J 13/06* (2013.01); *A01N 25/28* (2013.01); *A23L 27/72* (2016.08); *A23L 33/10* (2016.08); *A23L 33/30* (2016.08); *A61K 8/11* (2013.01); *A61K 8/8147* (2013.01); *A61K 8/84* (2013.01); *A61K 9/5026* (2013.01); *A61K 9/5031* (2013.01); *A61K 9/5089* (2013.01); *A61K 9/5094* (2013.01); *B01J 13/10* (2013.01); *C11D 3/505* (2013.01); *A61K 2800/412* (2013.01); *A61K 2800/56* (2013.01)

(58) Field of Classification Search
CPC ..... A01N 25/28; A61K 9/5026; A61K 9/5031
See application file for complete search history.

(56) References Cited

U.S. PATENT DOCUMENTS 4,898,780 A * 2/1990 Seitz ................... B01J 13/10
106/31.16
2003/0219384 A1* 11/2003 Donath ................ A61K 9/5026
424/9.6
(Continued)

OTHER PUBLICATIONS

Kenji Kono et al., pH-responsive permeability of poly(acrylic acid)-poly(ethylenimine) complex capsule membrane, Sep. 23, 1992, Journal of membrane science, 76 (1993) 233-243.*
(Continued)

*Primary Examiner* — John Pak
(74) *Attorney, Agent, or Firm* — BakerHostetler

(57) ABSTRACT

Polyelectrolyte microcapsules, and methods for making and using the polyelectrolyte microcapsules, are described. A method of making polyelectrolyte microcapsules includes forming an "interfacial complexation in emulsion" (ICE), wherein a polyelectrolyte "shell" is formed by complexing two different polyelectrolytes together at an interface between two immiscible fluids. Both hydrophilic and hydrophobic materials can be incorporated into the cores and shells of the polyelectrolyte microcapsules.

16 Claims, 7 Drawing Sheets

(51) Int. Cl.
| | |
|---|---|
| A61K 9/50 | (2006.01) |
| A61K 8/11 | (2006.01) |
| A61K 8/81 | (2006.01) |
| A61K 8/84 | (2006.01) |
| A23L 33/10 | (2016.01) |
| A23L 33/00 | (2016.01) |
| C11D 3/50 | (2006.01) |
| A23L 27/00 | (2016.01) |
| B01J 13/10 | (2006.01) |

(56) References Cited

U.S. PATENT DOCUMENTS

| | | | |
|---|---|---|---|
| 2006/0121122 A1* | 6/2006 | Nakajima | A61K 9/5089 424/490 |
| 2011/0014235 A1* | 1/2011 | Berninger | A61K 39/39 424/246.1 |
| 2014/0314839 A1* | 10/2014 | Vetro | A61K 38/1725 424/451 |

OTHER PUBLICATIONS

Qifeng Wang, Single and multicompartment hollow polyelectrolyte complex microcapsules by one step spraying, Feb. 11, 2015, Advanced materials, 2015, 27, 2077-2082.*

Fukui, Y. et al., "Preparation of monodispersed polyelectrolyte microcapsules with high encapsulation efficiency by an electrospray technique," Colloids and Surfaces A: Physiochemical and Engineering Aspects, vol. 370(1-3), pp. 28-34 (2010).*

Chen, H. et al., "Combined chemo-and photo-thermal therapy delivered by multifunctional theranostic gold nanorod-loaded microcapsules," Nanoscale, vol. 7, 8884-8897 (Apr. 10, 2015).*

Zhang et al., "One-Step Fabrication of Supramolecular Microcapsules fro Microfluidic Droplets", Science, 2012, vol. 335, pp. 690-694.

Kamat et al., "Engineering Polymersome Protocells", The Journal of Physical Chemistry, 2011, vol. 2, pp. 1612-1623.

Tiourina et al., "Artificial Cell Based on Lipid Hollow Polyelectrolyte Microcapsules: Channel Reconstruction and Membrane Potential Measurement", J. Membr. Biol., 2002, vol. 190, pp. 9-16.

Kolmakov et al., "Desiging communicating colonies of biomimetic microcapsules", Proc, Natl. Aced, Sci, USA, 2010, vol. 107, pp. 12417-12422.

Martino et al,, "Protein Expression, Aggregation, and Triggered Release from Polymersomes as Artificial Cell-like Structures", Agnew. Chem,, Int. Ed., 2012, vol. 51, pp. 6416-6420.

Caruso et al., Nanoengineering of Inorganic and Hybrid Hollow Spheres by Colloidal Templating, Science, Nov. 6, 1996, vol. 282, pp. 1111-1114.

Donath et al., "Novel Hollow Plymer Shells by Colloid-Templated Assembly of Polyelectrolytes", Agnew Chem. Int. Ed., 1996, vol. 37, pp. 2201-2205.

Wang et al., "Nanoporous Polyelectrolyte Spheres Prepared by Sequentially Coating Sacrificial Mesoporous Silica Spheres", Agnew. Chem., 2005, vol. 117, pp. 2948-2952.

Richardson et al., "Immersive Polymer Assembly on Immobilized Particles for Automated Capsule Preparation", Advanced Materials, 2013, vol. 25, pp. 6874-6878.

Wang et al., "Single- and Multicompartment Hollow Polyelecyrolyte Complex Microcapsules by One-Step Spraying", Advanced Materials, 2015, vol. 27, pp. 2077-2082.

Richardson et al., Preparation fo Nano- and Microcapsules by Electrophoretic Polymer Assembly, Angew. Chem. Int. Ed., 2013, vol. 52, pp. 6455-6458.

Li et al, "Pickering-Emulsion-Templated Encapsulation of a Hydrophilic Amine and Its Enhanced Stability Using Poly (allyl amine)", ACS Macro Lett., 2014, vol. 3, pp. 976-980.

Tong et al., "Stable Weak Polyelectrlyte Microcapsules with pH-Responsive Permeability", Macromolecules, 2006, vol. 39, pp. 335-340.

Mauser et al., "Balance of Hydrophobic and Electrostatic Forces in the pH Response o Weak Polyelectrolyte Capsules", Journal of Physical Chemistry, 2006, vol. 110, pp. 20246-20253.

Usov et al., "Dextran Coatings for Aggregation Control of Layer-by-Layer Assembled Polyelectrolyte Microcapsules", Langmuir, 2015, vol. 26, No. 15, pp. 12575-12584.

Shiratori et al., "pH-Dependent Thickness Behavior of Sequentially Adsorbed Layers of Weak Polyelectrolytes", Macromolecules, 2000, vol. 33, pp. 4213-4219.

Mendelsohn et al., "Rational Design of Cytophilic and Cytophobic Polyelectrolyte Multilayer Thin Films", Biomacromolecules, 2004, vol. 4, pp. 96-106.

Chung et al., "Methods of Loading and Releasing Low Molecular Weight Cationic Molecules in Weak Polyelectrolyte Multilayer Films", Langmuir, 2002, vol. 18, pp. 1176-1183.

Tong et al., "Layer-by-layer assembly of microcapsules and their biomedical applications", Chem. Soc. Rev., 2012, vol. 41, pp. 6103-6124.

Antipov et al., Polyelectrolyte multilayer capsule permeability control, Ciolloids and Surfaces A: Physiocochemical and Engineering Aspects, 2002, vol. 198-200, pp. 535-541.

Robertson et al., "Molecular Insights in the Structure and Layered Assembly of Polyelectrolytes at the Oil/Water Interface", The Journal of Physical Chemistry, 2014, vol. 118, pp. 28331-28343.

Windbergs et al., "Biodegradable Core-Shell Carriers for Simultaneous Encapsulation of Synergistic Actives", Journal of the American Chemical Society, vol. 135, pp. 7933-7937.

Lu et al., "Magnetic Nanoparticles: Synthesis, Protection, Functionalization and Application", Agnew. Chem. Int. Ed., 2007, vol. 56, pp. 1222-1244.

Park et al., "Synthesis Monodisperse Spherical Nanocrystals", AGnew. Chem. Iint. Ed., 2007, vol. 46, pp. 4630-4660.

Wu et al., "Autonomous Movement of controllable Assembled Janus Capsule Motors", ACS Nano, 2012, vol. 6, No. 12, pp. 10910-10916.

Hribar et al., "Enhanced Release of Small Molecules from Near-Infrared Light Responsive Polymer—Nanorod Composites", ACS Nano, 2011, vol. 5, No. 4, pp. 2948-2956.

Charati et al., "Light-Sensitive Polypeptide Hydrogel and Nanorod Composites", Small, 2010, vol. 6, No. 15, pp. 1608-1611.

You et al., "Near-Infrared Light Triggers Release of Paclitaxel from Biodegradable Micropheres: Photothermal Effect and Enhanced Antitumor Activity", Small, 2010, vol. 6, No. 9, pp. 1022-1031.

Kuo et al., "Multiple Release Kinetics of Targeted Drug from Gold Nanorod Embedded Polyelecyrolyte Conjugates Induced by Near-Infrared Laser Irradiation.", J. Am Chem. Soc., 2010, vol. 132, pp. 14163-14171.

Sau et al., "Seeded High Yield Synthesis of Short Au Nanorods in Aqueous Solution", Langmuir, 2014, vol. 20, pp. 6414-6420.

Cohen et al., Controlled Delivery Systems for Proteins Based on Poly(Lactic/Glycolic Acid) Microspheres, Pharmaceutical Research, vol. 8, No, 6, 1991, pp. 713-720.

Decher et al., "Multilayer Thin Films: Sequential Assembly of Nanocomposite Materials", John Wiley & Sons, 26 pages.

Decher et, al., "Buildup of Ultrathin Multilayer Films by a Self-Assembly Process, 1 consecutive Adsorption of antonic and Catonic Bipolar Amphiphiles on Charged Surfaces", Macromol. Chem., Macromol, Symp, vol. 46, pp. 321-327.

De Geest, et al., "The Pros and cons of Polyelectrolyte Capsules in Drug Delivery", Expert Opinion Drug Delivery, vol. 6, No. 6, pp. 613-624.

Rasmussen et al., "Bridging Nonliving and Living Matter", Artifical Life, vol. 9, pp. 269-316.

Zacharia of al., "Large-Scale Solvent Driven Actuation of Polyelectrolyte Multilayers Based on Modulation of Dynamic Secondary Interactions", ACS Appl. Mater. Interfaces, vol. 7, pp. 1848-1858.

Ammala, "Biodegradable polymers as encapsulation materials for cosmetics and personal care markets", International Journal of Cornetic Science, 2013, vol. 35, pp. 113-124.

(56) References Cited

OTHER PUBLICATIONS

Chang, Semipermeable Microcapsules. Science 146, 1964, pp. 524-525.
DeKoker et al., "Polymeric multilayer capsules delivering biotherapeutics", Advanced Drug Delivery Reviews, 2011, vol. 63, pp. 748-761.
Peyratout et al., "Tailor-Made Polyelectrolyte Microcapsules: From Multilayers to Smart Containers", Angewandte Chemie International Edition, 2004, vol. 43, pp. 3762-3783.
Esser-Kahn et al., "Triggered Release From Polymer Capsules", 2011, Macromolecules, vol. 44, pp. 5539-5553.
Gao et al., Swelling and Shrinking of Polyelectrolyte Microcapsules in Response to Changes in Temperature and Ionic Strength. Chemistry European Journal 9, 915-920 (2003).
Levy et al., "Polymer Microcapsules with Carbohydrate-Sensitive Properties", Advanced Functional Materials 1vol. 8, 2008, pp. 1586-1594.
Stoychev et al., "Self-folding all-polymer thermoresponsive microcapsules", Soft Matter vol. 7, 2011, pp. 3277-3279.
Bird et al,, "Tuning the properties of pH-responsive and redox sensitive hollow particles and gels using copolymer composition", Soft Matter 2012, vol. 8, pp. 1047-1057.
Yi et al., "Externally Triggered Dual Function of Complex Microcapsules," ACS Nano 2013, vol. 7, No. 10, pp. 8693-8705.
Liang K, et al. "Endocytic pH-Triggered Degradation of Nanoengineered Multilayer Capsules," Advanced Materials, 2014, vol. 26, pp. 1901-1905.
Delcea et al., Stimuli-responsive LbL capsules and nanoshells for drug delivery,. Advanced Drug Delivery Reviews, 2011, vol. 63, pp. 730-747.
De Geest et al., "Release mechanisms for polyelectrolyte capsules," Chemical Society Reviews, 2007, vol. 36, pp. 636-649.
Iler R., "Multilayers of Colloidal Particles," Journal of Colloid and Interface Science, 1966, vol. 21, pp. 569-594.
Bagaria HG, Wong MS, "Polyamine-salt aggregate assembly of capsules as responsive drug delivery vehicles," Journal of Materials Chemistry, 2011, vol. 21, pp. 9454-9466 2011.
Murthy et al., Polyamine-Guided Synthesis of Anisotropic, Multicompartment Microparticles, ACS Applied Materials & Interfaces, 2009, vol. 1, No. 3, pp. 590-596.
Murthy, et al., "Nanoparticle-Assembled Capsule Synthesis: Formation of Collidal Polyamine—Salt Intermediates", Journal of Physical Chemistry B, 2006, vol. 110, pp. 26619-25627.
Caruso, Nanoengineering of Particle Surfaces, Advanced Materials, 2001, vol. 13, No. 1, pp. 11-22.
Kantak et al., "A microfluidic pinball' for on-chip generation of Layer-by-Layer polyelectrolyte microcapsules", Lab Chip, 2011, vol. 11, pp. 1030-1035.
Ejima et al., "One-Step Assembly of Coordination Complexes for Versatile Film and Particle Engineering", Science, Jul. 12, 2013, vol. 341, pp. 154-157.
Richardson et al., "Fluidized Bed Layer-by-Layer Microcapsule Formation", Langmuir, 2014, vol. 30 pp. 10028-10034.
Wang et al., "Encapsulation of Water-Insoluble Drugs in Polymer Capsules Prepared Using Mesoporous Silica Templates for Intracellular Drug Delivery", Advanced Materials, 2010, vol. 22, pp. 4293-4297.
Mohanta et al., "Layer-by-Layer Assembled Thin Films and Microcapsules of Nanocrystalline Cellulose for Hydrophobic Drug Delivery", ACS Applied Materials & Interfaces, 2014, vol. 6, pp. 20093-20101.
Fu et al., "Extruded Superparamagnetic Saloplastic Polyelectrolytes Nanocomposites", ACS Applied Materials & Interfaces, 2014, vol. 7, p. 895-901.
Monteillet et al., "Charge-driven co-assembly of polyelectrolyes across oil-water interfaces", Soft Matter, 2013, vol. 9, pp. 11270-11275.
Kaufman et al., "Single-step microfluidic fabrication of soft monodisperse polyelectrolyte microcapsules by interfacial complexation", Lab Chip, 2014, vol. 14, pp. 3494-3497.

De Silva et al., "Simple Preparation of Polyelectrolyte Complex Beads for the Long-Term Release of Small Molecules", Langmuir, 2014, vol. 30, pp. 8915-8922.
Morita et at, "Protein encapsulation into biodegradable micropheres by a novel S/O/W emulsion method using poly (ethylene glycol) as a protein micronization adjuvant", Journal of Controlled Release, 2000, vol. 69, pp. 435-444.
Min et al., "Catechol-Modified Polyions in Layer-by-Layer Assembly to Enhance Stability and Sustain Release of Biomolecules: A Bioinspired Approach", Chemistry of Materials, 2011, vol. 23, pp. 5349-5357.
Zacharia et at, "Large-Scale Solvent Driven Actuation of Polyelectrolyte Multilayers Based on Modulation of Dynamic Seconedary Inactions", ACS Applied Materials & Interfaces, 2015, vol. 7, pp. 1848-1858.
Choi et at, "Influence of the Degree of Ionization on Weak Polyelectrolyte Multilayer Assembly", Macromolecules, 2005, vol. 38, pp. 116-124.
Lee et al., "Harnessing Interfacial Phenomena to Program the Release Properties of Hollow Microcapsules", Advanced Functional Materials, 2012, vol. 22, pp. 131-138.
Shum et al., "Double Emulsion Templated Monodisperse Phospholipid Vesicles", Langmuir, 2008, vol. 24, pp. 7651-7653.
Shum et al., "Dewetting-induced Membrane Formation by Adhesion of Amphiphile-Laden Interfaces", Journal of the American Chemical Society, 2011, vol. 133, pp. 4420-4426.
Hayward et al., "Dewetting Instability during the F or mation of Polymersomes from Block-Copolymer-Stabilized Double Emulsions", Langmuir, 2006, vol. 22, pp. 4457-4461.
Hotan Mojarradi, "Coupling of substances containing a primary amine to hyaluronian via carbodiimide-mediated amidation", Master Thesis, 2011, 49 pages.
Mansuroglu et al., "Characterization of water-soluble conjugates of polyacrylic acid and antigenic peptic of FMDV by size exclusion chromatogaphy with quadruple detection", Materials Science and Engineering, 2012, vol. C32, pp. 112-118.
Palacci et al.,"Living Crystals of Light-Activated Colloidal Surfers", Science, 2013, vol. 339, pp. 936-940.
Dejugnat et al., "pH-Responsive Properties of Hollow Polyelectrolyte Microcapsules Templated on Various Cores", Langmuir, 2004, vol. 20, pp. 7265-7269.
Hauser et al., "Reversible pH-Dependent Properties of Multilayer Microcapsules Made of Weak Polyelectrolytes", Macromolecular Rapid Communications, 2004, vol. 25, pp. 1781-1785.
Caruso et al., "Magnetic Nanocomposite Particles and Hollow Spheres Constructed by a Sequential Layering Approach", Chemistry of Materials, 2001, vol. 13, pp. 109-116.
Caruso et al., "Multilayered Titania, Silica, and Laponite Nanoparticle Coatings on Polystyrene Colloidal Templates and Resulting Inorganic Hollow Spheres", Chemistry of Materials, 2001, vol. 13, pp. 400-409.
Antipov et al., "Sustained Release Properties of Polyelectrolye Multilayer Capsules", Journal of Physical Chemistry B, 2001, vol. 105, pp. 2281-2284.
Caruso et al., "Enzyme Encapsulation in Layer-by-Layer Engineered Polymer Multilayer Capusles", Langmuir, 23000, vol. 16, pp. 1485-1488.
Wang et al., "Encapsulation of Water-Insoluble Drugs in Polymer Capsules Prepared Using Mesoporous Silica Templates for Intracellular Drug Delivery", Advanced Materials, 2010, vol. 22, pp. 4293-4297. 2010.
Wang et al., "Nanoporous Polyelectrolyte Spheres Prepared by Sequentially Coating Sacrificial Mesoporous Silica Spheres", Angewandte Chemie-International Edition, 2005, vol. 44, pp. 2888-2892.
Chen et al., "The Emergence of Competition Between Model Protocells", Science, 2004, vol. 305, pp. 1474-1476.
Holden et al., "Functional Bionetworks from Nanoliter Water Droplets", Journal of the American Chemical Socitty, 2007, vol. 129, pp. 8650-8655.
Mansy et al., "Template-directed synthesis of a genetic polymer in a model protocell", Nature, 2008, vol. 454, pp. 122-U10.

(56) References Cited

OTHER PUBLICATIONS

Peter J. Wilde, "Eating for Life: Designing Foods for Appetite Control", Journal of Diabetes Science and Technology, 2009, vol. 3, Issue 2, pp. 366-370.
Tu et al., "Controlling the Stability and Size of Double-Emulsion-Templated Poly(lactic-co-glycolic) Acid Microcapsules", Langmuir, 2012, 28(26), pp. 9944-9952.

\* cited by examiner

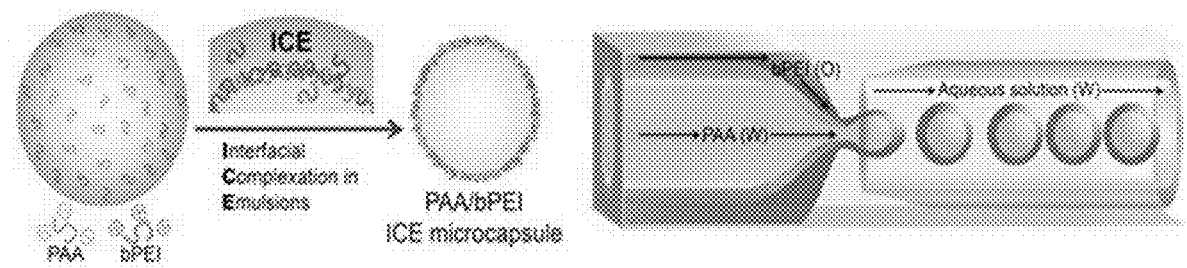
Fig. 1A
Fig. 1B
Fig. 2A
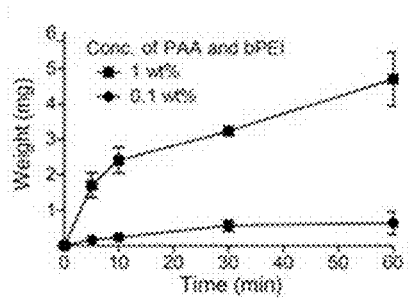
Fig. 2B
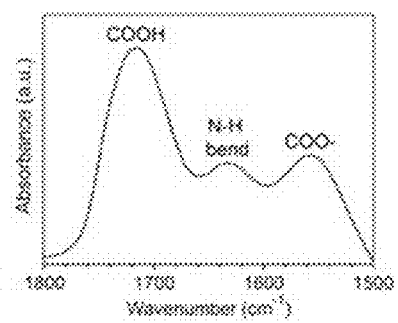
Fig. 2C

Fig. 3B                    Fig. 3C

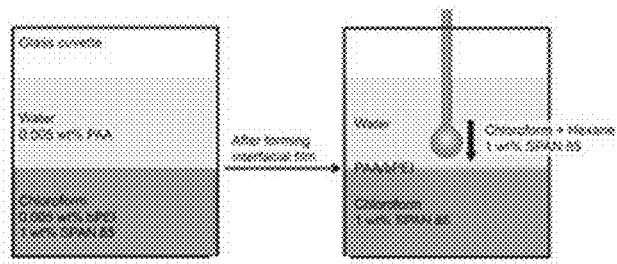
Fig. 5A
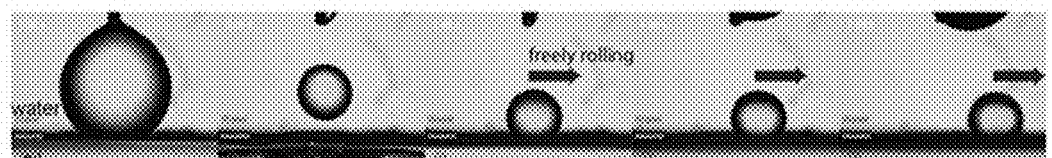
Fig. 5B
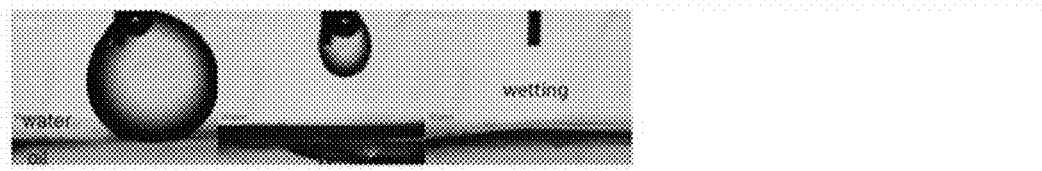
Fig. 5C
Fig. 6

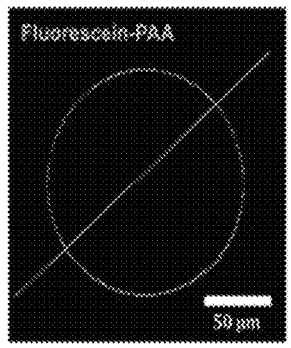 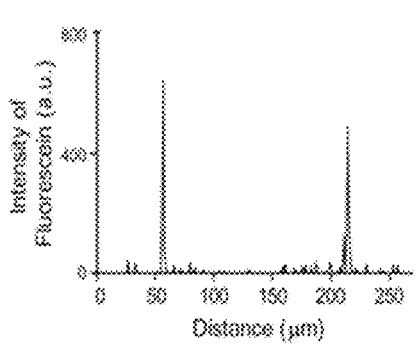 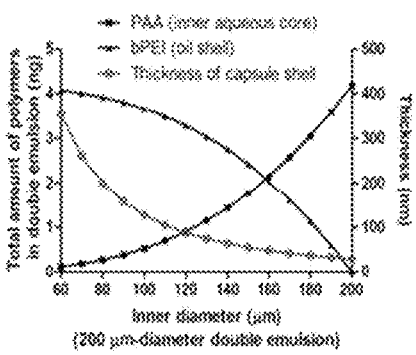
Fig. 7A     Fig. 7B
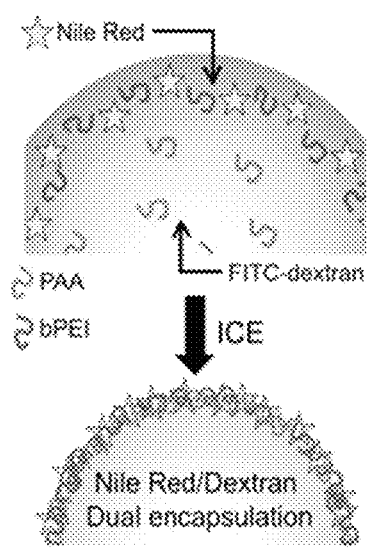 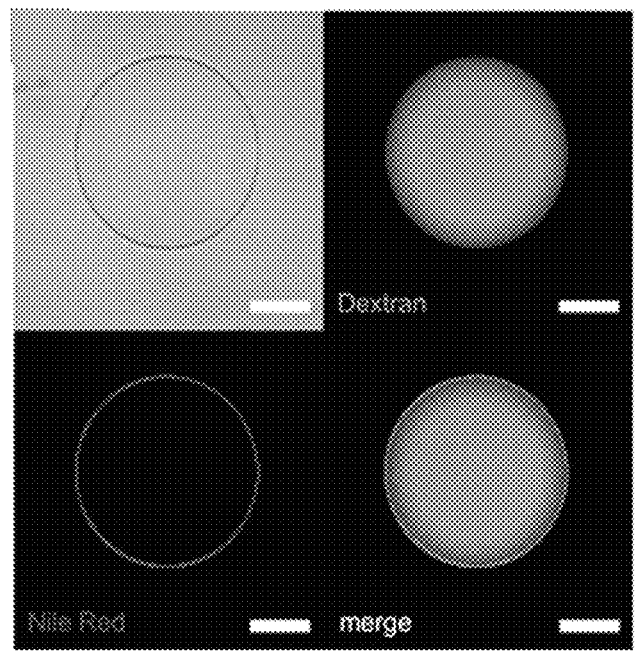
Fig. 8A     Fig. 8B

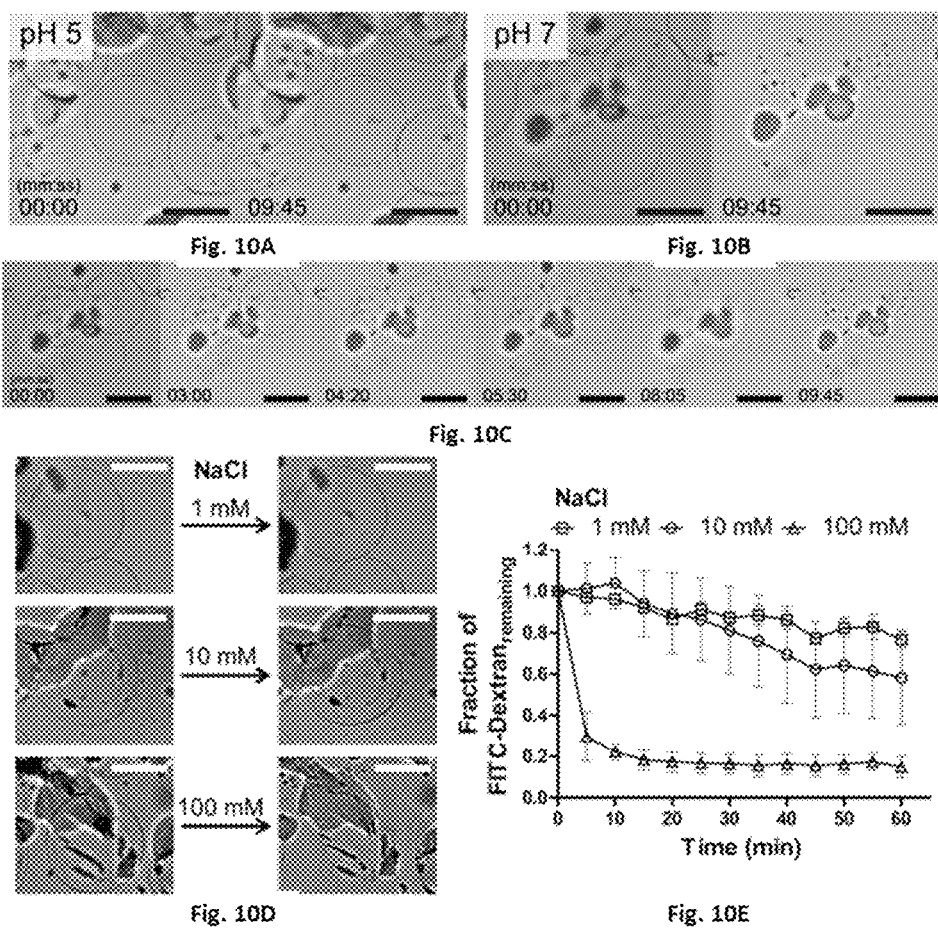
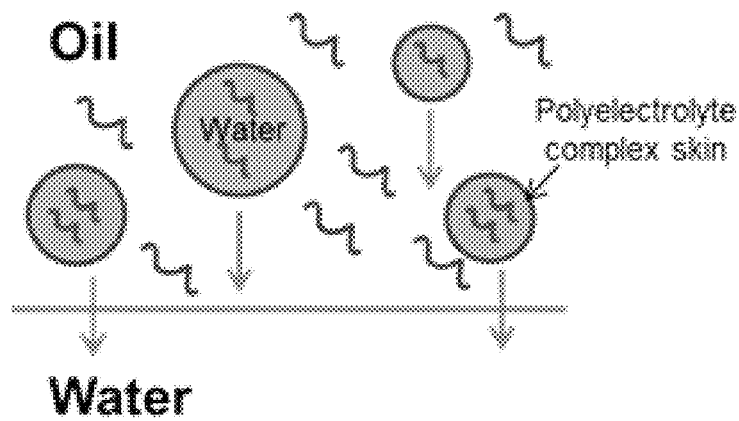
Fig. 11

POLYELECTROLYTE MICROCAPSULES AND METHODS OF MAKING THE SAME

CROSS REFERENCE TO RELATED APPLICATIONS

This application claims priority to U.S. Provisional Application No. 62/146,586, entitled POLYELECTROLYTE MICROCAPSULES AND METHODS OF MAKING THE SAME, filed Apr. 13, 2015, the contents of which are incorporated by reference herein in their entirety.

STATEMENT REGARDING FEDERALLY SPONSORED RESEARCH

This invention was made with government support under grant number 1120901 awarded by the National Science Foundation. The government has certain rights in the invention.

FIELD OF THE INVENTION

Embodiments of the present invention relate to polyelectrolyte microcapsules, and methods of making and using the polyelectrolyte microcapsules. In particular, embodiments of the present invention relate to a method for generating polyelectrolyte microcapsules with high encapsulation efficiency and the ability to incorporate both hydrophilic and hydrophobic active agents.

BACKGROUND OF THE INVENTION

Microcapsules that encapsulate and protect molecules and materials by forming isolated aqueous compartments inside hollow shells are widely used in a variety of applications in the food, pharmaceutical, cosmetics and agriculture industries. In addition to the protection of encapsulated materials, microencapsulation enables a delayed, controlled and/or triggered release of active ingredients from the capsule, which can be induced by various stimuli. Microcapsules made of polyelectrolytes, in particular, offer a number of advantages that make them ideal for applications in microencapsulation and controlled/triggered release of active agents due to their tendency to drastically change their degree of ionization and conformation in response to changes in the solution pH and ionic strength. Interactions between two oppositely charged polymers can be modulated to induce abrupt phase transitions or even disassembly of complex structures, leading to triggered rupture of microcapsules.

Polyelectrolyte microcapsules can be generated using a variety of methods. Two representative approaches that have shown great promise in generating stimuli-responsive polyelectrolyte microcapsules are layer-by-layer (LbL) assembly and polyamine-salt aggregation (PSA). The LbL method is a versatile technique that enables the formation of polyelectrolyte microcapsules by the sequential deposition of molecularly thin layers of polyelectrolytes on sacrificial template particles. Because of this control at the molecular level, polyelectrolyte multilayers with a wide range of compositions, properties and functionality can be prepared. The PSA method relies on mixing a polyelectrolyte (typically a polyamine) with an oppositely charged multivalent ion under appropriate conditions, which leads to the solution-phase self-assembly of these two molecules into stimuli-responsive microcapsules. With these approaches, by choosing an appropriate set of materials and varying the assembly conditions such as pH and ionic strengths of the solutions, microcapsules with useful functionality, such as stimuli responsiveness and biocompatibility, can be prepared.

Although useful properties of microcapsules prepared using these approaches have been demonstrated, the low encapsulation efficiency of these methods is a major hindrance to their widespread application. While approaches to enhance encapsulation efficiency by using sacrificial porous particles have been developed for LbL assembly, LbL microcapsule preparation tends to be extremely tedious and time consuming. In addition, it is difficult to incorporate both hydrophobic and hydrophilic species into these polyelectrolyte microcapsules, which may be important for a number of applications. Thus, there remains a need for methods of generating polyelectrolyte microcapsules with high encapsulation efficiency and the ability to incorporate both hydrophilic and hydrophobic active agents.

SUMMARY OF THE INVENTION

An embodiment of the present invention relates to a method of making polyelectrolyte microcapsules comprising:
forming an emulsion comprising an inner water phase and an oil phase,
wherein the inner water phase comprises a first polyelectrolyte and the oil phase comprises a second polyelectrolyte,
wherein the first and second polyelectrolytes form a polyelectrolyte complex at the interface between the water phase and oil phase, and wherein polyelectrolyte microcapsules are formed following a spontaneous dewetting process whereby the polyelectrolyte microcapsules separate from the oil phase.

Embodiments of the present invention also relate to a polyelectrolyte microcapsule comprising a core completely surrounded by a shell, wherein the shell comprises a complex of at least two polyelectrolytes, and wherein the core optionally comprises at least one active ingredient suspended in an aqueous solution. The shell may optionally comprise one or more hydrophobic active ingredients.

Embodiments of the present invention also relate to pharmaceutical compositions, agricultural compositions, cosmetic compositions and food products comprising the polyelectrolyte microcapsules.

BRIEF DESCRIPTION OF THE DRAWINGS

FIG. 1A provides a schematic illustration of an embodiment of a microfluidic device for generating W/O/W double emulsions.

FIG. 1B provides a conceptual illustration representing an embodiment of a one-step generation of polyelectrolyte microcapsules via the interfacial complexation in emulsion (ICE) method.

FIG. 2A provides a photo image showing interfacial complexes formed at a bulk interface between 1 wt % PAA solution (dissolved in deionized water, superphase) and 1 wt % bPEI solution (dissolved in chloroform, subphase) (scale bar: 1 cm).

FIG. 2B provides a graph showing the weight of PAA/bPEI interfacial complex as a function of time (the experiments were performed three times for each case; the error bars are standard deviations).

FIG. 2C provides an FTIR spectrum of a PAA/bPEI interfacial film.

FIG. 3B provides an optical image capturing the moment of separation of ICE microcapsules from oil droplets.

FIG. 3C provides an optical image showing the ICE microcapsules after discarding the separated oil droplets.

FIG. 5A provides a schematic illustration of wettability determination on an interfacial film.

FIG. 5B shows the behavior of an oil drop on a PAA/bPEI interfacial film.

FIG. 5C shows the behavior of an oil drop on a water-oil interface without film.

FIG. 6 is a table showing behaviors of double emulsions and dewetting phenomena depending on the solution pH of the continuous phase (collection solution). Scale bar=100 μm.

FIG. 7A (left) is a confocal microscopy image of (PAA/bPEI) ICE microcapsule made with fluorescently labeled PAA (Fluorescein-PAA) and (right) fluorescence intensity along the yellow straight line.

FIG. 7B shows an estimation of the upper limit of the dried shell thickness of (PAA/bPEI) ICE microcapsules generated from 200 μm-diameter double emulsion comprising 0.1 wt % PAA-inner aqueous core and 0.1 wt % bPEI-shell.

FIG. 8A is a schematic illustration describing dual encapsulation of a hydrophilic agent (FITC-dextran) and a hydrophobic agent (Nile red).

FIG. 8B provides confocal microscopy images showing an ICE microcapsule encapsulating FITC-dextran and Nile red in the core and shell of the capsule, respectively. Scale bar: 50 μm.

FIG. 10A provides optical images of ICE microcapsules showing pH-triggered responses at pH 5.

FIG. 10B provides optical images of ICE microcapsules showing pH-triggered responses at pH 7.

FIG. 10C provides sequential optical images of ICE microcapsules showing pH-triggered responses at pH 7.

FIG. 10D provides optical images of ICE microcapsules showing salt-triggered release; deformations of capsules in (top) 1 mM NaCl (middle) 10 mM NaCl and (bottom) 100 mM NaCl solutions, respectively. Duration=10 min., 20 sec.

FIG. 10E shows release profiles representing the relative fluorescence intensity of 4 kDa FITC-dextran remaining in ICE microcapsules normalized by initial fluorescence intensity under different NaCl concentrations. The error bars are standard deviations. Scale bar=100 μm.

FIG. 11 illustrates an embodiment of a method for making a water-in-oil emulsion above a macroscopic water-oil interface.

DETAILED DESCRIPTION OF THE INVENTION

Figure 3A:
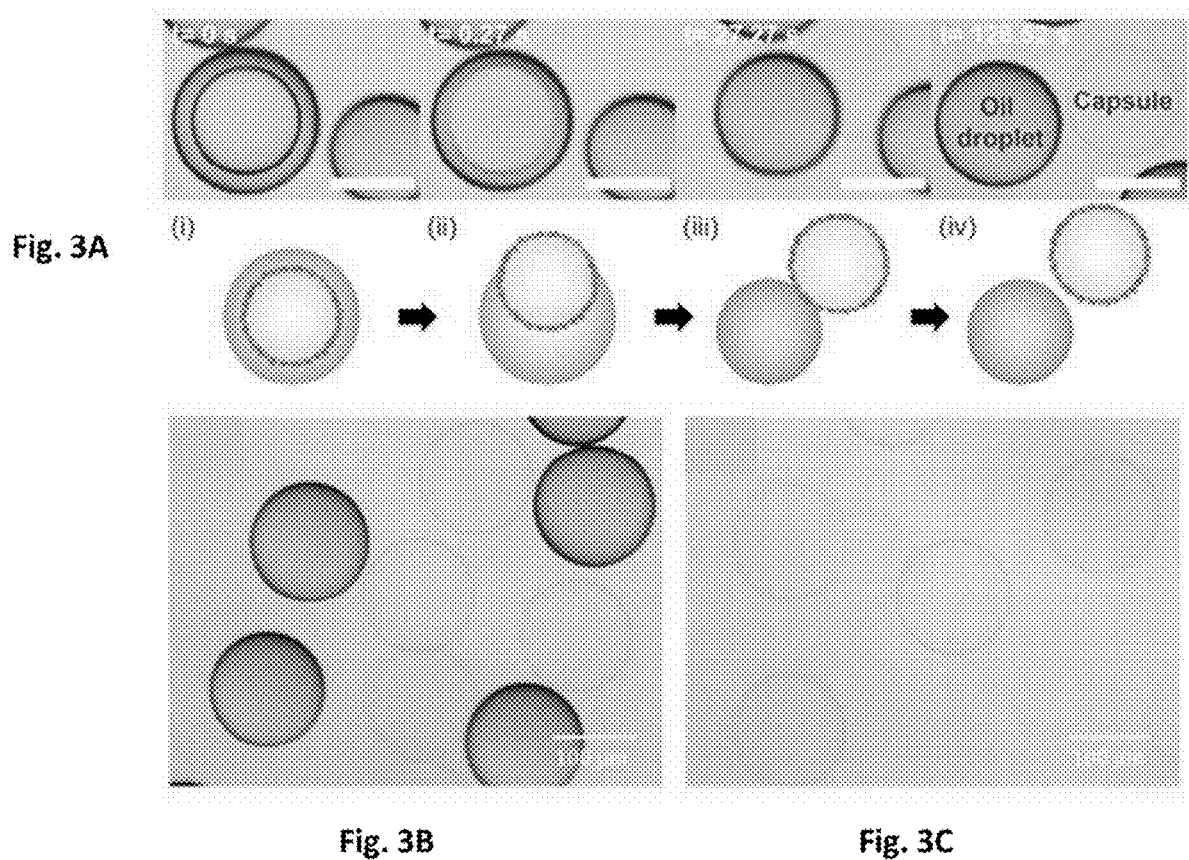
FIG. 3A (top) provides optical images showing generation processes of (PAA/bPEI) ICE microcapsules through complete dewetting and (bottom) schematic illustrations describing the formation process: i) double emulsion formation, ii) initiation of dewetting, iii) partial dewetting, and iv) complete dewetting (scale bar: 100 μm).

Polyelectrolyte microcapsules are extremely useful for encapsulation and triggered release applications. However, conventional preparation methods yield low encapsulation efficiency and are often time-consuming. Also, conventional methods do not allow for the encapsulation of hydrophobic materials. Two approaches that have been used to generate stimuli-responsive polyelectrolyte microcapsules are layer-by-layer (LbL) assembly and polyamine-salt aggregation (PSA).

For LbL assembly, oppositely charged polymers are sequentially deposited onto a sacrificial solid core to form polyelectrolyte complex-based coatings on the solid particle. Subsequently, the core particle is removed via dissolution to form a hollow microcapsule, and target encapsulants are subsequently introduced through the microcapsule shell by tuning its permeability to achieve microencapsulation. LbL assembly has low encapsulation efficiency because the approach involves core dissolution and subsequent introduction of materials into the microcapsule lumen through the shell. LbL assembly is also extremely tedious and time-consuming. These factors have limited the introduction of LbL-based microcapsules in practical applications. Another approach to produce polyelectrolyte microcapsules relies on mixing a polyelectrolyte (typically a polyamine) with an oppositely charged multivalent ion. This leads to the solution-phase self-assembly of these two molecules into hollow microcapsules. Although the LbL and PSA approaches provide complementary methods to create stimuli-responsive polyelectrolyte microcapsules that encapsulate aqueous cores, the low encapsulation efficiency of these methods is a major hindrance to their widespread application. Also, these methods do not enable incorporation of both hydrophobic and hydrophilic species into the microcapsules, which may be important for a number of applications.

Embodiments of the present invention provide methods of making polyelectrolyte microcapsules that comprise forming a polyelectrolyte "shell" by complexing two different polyelectrolytes together at an interface between two immiscible fluids (e.g., between an aqueous fluid and a hydrophobic organic fluid). The method may be referred to herein as an "interfacial complexation in emulsion" (ICE). Methods of the present invention can generate polyelectrolyte microcapsules with high encapsulation efficiency (see FIG. 1B and FIG. 8). Unlike conventional methods, embodiments of the present invention do not require a first step of forming a polyelectrolyte shell followed by the subsequent introduction of materials (e.g., active ingredients) into the microcapsule core through the shell. Instead, embodiments of the present invention may be considered "one-step" methods because active ingredients can be incorporated into the microcapsule core at essentially the same time that the shell and core are formed (i.e., during the formation of the interfacial complexation in emulsion). Thus, the active ingredients do not have to be introduced into the core after the core has been generated. Also, embodiments of the present invention provide a continuous process for generating the polyelectrolyte microcapsules (i.e., wherein the emulsion is formed continuously, instead of batch-wise). Such continuous methods render the methods much more scalable for industrial production compared to conventional methods. In accordance with particular embodiments, both hydrophilic and hydrophobic materials can be incorporated into the cores and shells of the polyelectrolyte microcapsules, respectively (FIGS. 8 and 9).

As used herein, a polyelectrolyte microcapsule of the present invention comprises a shell that can encapsulate one or more active ingredients inside the aqueous "core" that is completely surrounded by the shell. The shell comprises a complex of two or more different types of polyelectrolytes (i.e., a crosslinked polyelectrolyte layer). As used herein, a "polyelectrolyte" is a polymer, wherein the polymer bears electrolyte groups capable of ionic dissociation (i.e., the electrolyte groups are components or substituents of the polymer chain). Any suitable polyelectrolytes known in the art can be used in accordance with the invention. Non-limiting examples of polyelectrolytes suitable for use in accordance with the present invention include polyanions such as polyacrylic acid, polymethacrylic acid, poly(styrene sulfonate) and poly(vinyl sulfonate), and polycations such as poly(allylamine hydrochloride), polyvinylamine and poly (diallyldimethylammonium chloride).

The diameters or widths of the polyelectrolyte microcapsules preferably range from about 1 µm to about 300 µm, or about 1 µm to about 250 µm, or about 1 µm to about 200 µm, or about 1 µm to about 150 µm, or about 1 µm to about 100 µm, or about 1 µm to about 50 µm. The thickness of the shells preferably range from about 10 nm to about 10 um, or about 10 nm to about 5 µm, or about 10 nm to about 1 µm, or about 10 nm to about 500 nm, or about 10 nm to about 250 nm, or about 10 nm to about 100 nm. The polyelectrolyte microcapsules may have any shape but they are preferably spherical or substantially spherical.

In accordance with particular embodiments, microencapsulation enables a delayed, controlled and/or triggered release of active ingredients from the microcapsules, which can be induced by various stimuli from the surrounding environment. For example, polyelectrolytes can drastically change their degree of ionization and conformation in response to changes in solution pH and ionic strength, leading to triggered rupture of the microcapsules. Thus, the shells of the polyelectrolyte microcapsules of the present invention comprise materials that are responsive to outside stimuli, such as changes in solution and/or ionic strength, and they are not comprised of only solid, non-responsive materials. The shells of the polyelectrolyte microcapsules of the present invention are also capable of incorporating hydrophobic species (e.g., hydrophobic molecules and/or hydrophobic nanoparticles).

In accordance with particular embodiments, one or more active ingredient(s) are suspended in the aqueous phase that is completely surrounded by the solid shell. Active ingredients include biologically or chemically active compounds which have a qualitative or quantitative effect on chemical, biochemical, biophysical, or physiological processes.

For pharmaceutical applications, the active ingredient(s) may comprise one or more active pharmaceutical ingredients (APIs), wherein the polyelectrolyte microcapsules comprising the API are administered to a subject to treat a disease or condition, or one or more symptoms thereof. Embodiments of the present invention provide a pharmaceutical composition comprising one or more pharmaceutical carriers and polyelectrolyte microcapsules of the present invention.

For agricultural applications, the active ingredient(s) may comprise one or more herbicides, pesticides, or plant nutrients, wherein the polyelectrolyte microcapsules comprising the active ingredient(s) are administered to crops. Embodiments of the present invention provide an agricultural composition comprising one or more agricultural carriers and polyelectrolyte microcapsules of the present invention.

For cosmetic applications, the active ingredient(s) may comprise one or more antioxidants, anti-bacterial agents, or fragrances, wherein the polyelectrolyte microcapsules comprising the active ingredient(s) are applied to a subject's skin. Embodiments of the present invention provide a cosmetic composition comprising one or more cosmetic carriers and polyelectrolyte microcapsules of the present invention.

For food applications, the active ingredient(s) may comprise one or more foodstuffs, flavorants, nutrients, vitamins, or minerals, wherein the polyelectrolyte microcapsules comprising the active ingredient(s) are consumed by a subject (e.g., after being mixed into a food product). Embodiments of the present invention provide a food product comprising polyelectrolyte microcapsules of the present invention. In the food industry, microcapsules filled with aqueous compartments can be used to induce satiation upon intake by affecting the distension volume of the stomach. Many polymers that are used in food processing are edible FDA-approved polyelectrolytes (e.g., polysaccharides) that can be used in the ICE microcapsule formation.

Another advanced application of microcapsules involves encapsulation and release of self-healing agents to "self-repair" materials upon structural damages.

According to particular embodiments, polyelectrolyte microcapsules of the present invention can be functionalized with hydrophobic materials by their addition to the oil phase of the emulsion. Thus, in addition to hydrophilic agents that can be encapsulated in the core (or "lumen") of these microcapsules, hydrophobic agents and hydrophobic nanoparticles can be incorporated into the polyelectrolyte shell, providing additional opportunities for functionalization. Non-limiting examples of nanoparticles that are suitable for use in accordance with the present invention include $SiO_2$, $TiO_2$, $Fe_2O_3$, $Al_2O_3$, gold, silver etc. Non-limiting examples of other hydrophobic agents include dyes, drugs, conjugated polymers, etc. As used herein, a hydrophobic agent is a molecule, compound or material that is substantially water-insoluble (i.e., it lacks an affinity for water and is not readily miscible in water).

According to particular embodiments, the method comprises forming an emulsion between a hydrophilic "water phase" and a hydrophobic "oil phase," wherein the water phase comprises a first polyelectrolyte and the oil phase comprises a second polyelectrolyte. "Oil phase" or "oil" is understood to encompass any organic fluids that are hydrophobic and/or partially or fully immiscible with water. The first and second polyelectrolytes form a polyelectrolyte complex at the interface between the water phase and oil phase. This interfacial polyelectrolyte complexation, followed by a spontaneous dewetting phenomenon whereby the polyelectrolyte complex separates from the oil phase, leads to the formation of the polyelectrolyte microcapsules. Thus, the polyelectrolyte complex becomes the "shell" of the polyelectrolyte microcapsule that encapsulates a portion of the water phase (the inner aqueous "core").

The method may further comprise comprising dissolving the first polyelectrolyte in the inner water phase and dissolving the second polyelectrolyte in the oil phase prior to forming the emulsion. According to particular embodiments, the method further comprises adding at least one active ingredient to the inner water phase prior to forming the emulsion and/or adding one or more hydrophobic materials to the oil phase prior to forming the emulsion.

According to one embodiment, forming the emulsion of immiscible fluids comprises forming a water-in-oil-in-water (W/O/W) emulsion (for example, with the use of a microfluidics device as shown in FIG. 1B, and as described in the 2012 publication by Fuquan Tu and Daeyeon Lee, Controlling the Stability and Size of Double-Emulsion-Templated Poly(lactic-co-glycolic) Acid Microcapsules; Langmuir, 2012; 28(26): pp. 9944-9952, which is incorporated by reference herein, in its entirety and for all purposes. The microfluidics device is capable of generating the polyelectrolyte microcapsules in a continuous process instead of batch-wise, i.e., emulsions can be generated one after the other to continuously produce microcapsules, whereas a batch-wise process only generates one emulsion at a time. A water-in-oil-in-water (W/O/W) emulsion includes the inner water phase, the middle oil phase, and an outer water phase. According to particular embodiments, the method also comprises adding one or more additives to each phase prior to forming the emulsion (e.g., the inner water phase, the oil phase, and the outer water phase), wherein the additives are selected from the group consisting of stabilizing agents, surfactants, pH adjusters and combinations thereof. The method may further comprise adjusting the pH of the inner water phase, the oil phase, and/or the outer water phase prior to forming the emulsion.

Water-in-oil-in-water (W/O/W) double emulsions are preferably generated using a glass capillary microfluidic device (FIG. 1). To generate double emulsions, three different fluid phases are injected into the microfluidic device by three syringe pumps with controlled flow rates. According to particular embodiments, a glass capillary microfluidics device (see, e.g., FIG. 1) is utilized, wherein the inner "water phase" comprises water, a hydrophilic polyelectrolyte, and optionally one or more active ingredients and optionally one or more additives (e.g., stabilizers, pH adjusters, surfactants, etc.), the middle "oil phase" comprises a hydrophobic polyelectrolyte, optionally one or more hydrophobic active ingredients, and optionally one or more additives (e.g., stabilizers, pH adjusters, surfactants, etc.), and the outer phase comprises water and optionally one or more additives (e.g., stabilizers, pH adjusters, surfactants, etc.).

According to an alternative embodiment, forming the emulsion comprises forming a double emulsion using a conventional two-step emulsification (i.e., emulsifying water in oil to form a water-in-oil emulsion and emulsifying this water-in-oil emulsion in water, thereby forming a water-in-oil-in-water double emulsion). For example, by creating a water-in-oil emulsion above a macroscopic water-oil interface (see FIG. 11), it is possible to continuously generate polyelectrolyte microcapsules through interfacial complexation and spontaneous dewetting. It should be noted that these W/O/W methods are different from polyelectrolyte complexation at the interface of single water-in-oil (W/O) or oil-in-water (O/W) emulsions, which have led to the formation of polyelectrolyte complex layer covered emulsions. For example, methods of the present invention generate a water compartment dispersed in water, in contrast to prior methods that provide oil droplets covered with polyelectrolyte coacervate dispersed in water or vice versa.

According to particular embodiments, following the formation of the emulsion, it was surprisingly found that the inner aqueous cores begin protruding out of the oil droplets (FIG. 3A (i)-(iii)). The inner aqueous core does not merge with the outer (continuous) water phase during protrusion, due to the existence of the shell that is protecting the inner aqueous core. Eventually, the shell and inner core become polyelectrolyte microcapsules upon complete separation of the inner cores from the oil phase (FIG. 3A (iv) and FIG. 3B). The protrusion and subsequent separation of the microcapsules from the oil phase is referred to herein as a "dewetting process." Preferably, the dewetting process occurs spontaneously following the formation of the emulsion (i.e., no action is required by the operator to separate the microcapsules from the oil phase).

According to particular embodiments, the method of the present invention further comprises collecting the polyelectrolyte microcapsules after they separate from the oil phase. Oil droplets float so it is very easy to physically separate the microcapsules from the oil droplets according to known methods.

The embodiments of the invention are described above using the term "comprising" and variations thereof. However, it is the intent of the inventors that the term "comprising" may be substituted in any of the embodiments described herein with "consisting of" and "consisting essentially of" without departing from the scope of the invention. Unless specified otherwise, all values provided herein include up to and including the starting points and end points given.

The following examples further illustrate embodiments of the invention and are to be construed as illustrative and not in limitation thereof.

EXAMPLES

Example 1

Characterization of an Interfacial Complexation Between PAA and bPEI

Before making ICE microcapsules from double emulsions, the interfacial complexation of two polymers at the interface between two immiscible fluids was observed. The two model polymers used for this study were poly(acrylic acid) (PAA) and branched poly(ethyleneimine) (bPEI), as they have been extensively used to prepare polyelectrolyte microcapsules via LbL assembly. Also, the degree of ionization of these two polymers depends strongly on the solution pH (i.e., they are weak polyelectrolytes), so they offer the potential to tune the properties of microcapsules via pH control. It was found that branched poly(ethylenimine) (bPEI) containing primary, secondary and tertiary amines readily dissolves in pure chloroform as well as in mixtures of chloroform and hexane. When an interface was formed between a PAA-containing aqueous phase and bPEI-containing chloroform, the formation of a film at the interface was immediately observed (FIG. 2A). The amount of polyelectrolyte complex increased with time and the concentrations of the polymers, indicating that this layer grows continuously through the diffusion and complexation of the two polymers at the interface (FIG. 2B).

To understand the molecular driving force for the formation of the PAA/bPEI interfacial complex, the charge state of PAA using Fourier transform-infrared spectroscopy was analyzed. The FTIR spectrum of the interfacial complex (FIG. 2C) showed two distinct peaks related to PAA: one at 1716 $cm^{-1}$, corresponding to the carboxylic acid (COOH), and the other at 1553 $cm^{-1}$, corresponding to the ionized carboxylate (COO—). The degree of ionization of PAA in the interfacial film was about 30%, which suggests that the driving force for complexation is electrostatic in nature. It should be noted that the pH of the inner aqueous phase was pH 3.7. Given that the pKa of PAA in solution was reported to be 5.5-6.0 and the degree of ionization of PAA at pH 3.7 in solution was about 5%, it was surprising that the degree of PAA ionization in the interfacial complex film was much greater than that in a pH 3.7 solution. Without being bound by any theory, it is believed that the amine groups of bPEI in the oil phase become protonated as they encounter the acidic aqueous phase. In addition, the protonation of the amine groups of bPEI can be induced by the deprotonation of carboxylic acid groups of PAA and subsequent transfer of protons from PAA to bPEI. In turn, the complexation of oppositely charged functional groups would lead to the formation of an the ionically crosslinked polyelectrolyte complex layer at the water-oil interface. The ionization of PAA in the interfacial complex layer, despite the low pH condition (pH 3.7,) is analogous to an increase in the degree of ionization of PAA in the layer-by-layer films relative to the solution value at a given pH. This shift in the apparent pKa of PAA was attributed to the lowered energy barrier for the ionization of PAA in the presence of positively charged functional groups; it is believed that an analogous mechanism is responsible for the ionization of PAA and in turn the electrostatically-assisted interfacial complexation at the inner water-oil interface.

Example 1 Methods

Synthesis and Characterization of Macroscopic Polyelectrolyte Complexes 0.1 wt % and 1 wt % polyelectrolyte solutions were used to form interfacial films in 2-cm diameter glass vials. To make polymer solutions, poly(acrylic acid) (PAA, Polyscience, 25% solution, Mw: 345,000 g/mol) dissolved in deionized water and branched poly (ethyleneimine) (bPEI, Sigma-Aldrich, Mw: 25,000 g/mol) dissolved in chloroform (Fisher Scientific) were used. In the case of PAA solutions (both 0.1 and 1 wt %), their pH was adjusted to pH 3.7. Also, because SPAN 85 (Sigma-Aldrich) were used as surfactants in the double emulsion experiment, 1 wt % of SPAN 85 (sorbitan trioleate, CAS No.: 26266-58-0) was added in chloroform. Concentrations of each polymer solution were adjusted so that their mole ratio was in a ratio of 1:1 and 3 mL of each solution were added in a vial. Interfacial complexes were harvested at interfaces using a pair tweezers at 5, 10, 30 and 60 min and washed with pH 2 water. After drying the films for 1 day, their weights were measured using an electronic balance.

FTIR spectrum of a macroscopic interfacial complex film was recorded using an FTIR spectrometer (Thermo Nicolet 6700 FT-IR Spectrometer). To prepare samples mimicking the shell of the ICE microcapsule, the same condition was used (oil phase: chloroform, 0.1 wt % bPEI, 1 wt % SPAN 85; aqueous phase: 0.1 wt % PAA, pH 3.7) that was used for forming interfacial films in the bulk system (FIG. 2A). The use of chloroform as the oil phase ensured the formation of a planar interface, facilitating the characterization of the interfacial film. The interfacial films were harvested after 5 minutes and gently washed with pH 2 solution several times. Subsequently, the film was dried under vacuum overnight. Finally, to prepare a sample for FTIR spectroscopy, a dried PAA/bPEI interfacial film was mixed with KBr powder and compressed to form a pellet.

To determine the wettability of the interfacial complex layer, glass cells (Starna Cells. Inc., 96-G-20, W·L·H: 28 mm·26 mm·40 mm) and a goniometer (Rame-Hart model 200) were used. Oil phase was made with chloroform and bPEI (0.005 wt %), and aqueous phase was 0.005 wt % PAA solution (pH 3.7). After forming a planar interfacial film between the oil and water phases for 1 hour at room temperature, an oil droplet containing a mixture of chloroform (50 v/v %), hexane (50 v/v %) and SPAN 85 (1 wt %) was placed at the interface using a syringe needle.

Example 2

Generation of (PAA/bPEI) ICE Microcapsule Using Double Emulsion System

Next, a microfluidic water-in-oil-in-water (W/O/W) emulsion was used to prepare ICE microcapsules as illustrated in FIG. 1B. To aid in the stabilization of these double emulsions, poly(vinyl alcohol) (PVA) and SPAN 85 were added to the outer aqueous and middle oil phases, respectively. A mixture of chloroform and hexane in a volume ratio of 1:1 was used as the middle phase (the use of pure chloroform as the oil phase typically does not lead to the formation of stable double emulsions). Using these combinations, stable PAA aqueous core-bPEI oil shell double emulsions were formed.

Surprisingly, instead of W/O/W double emulsions becoming polyelectrolyte microcapsules via gradual and complete evaporation of the solvents from the middle phase, the inner aqueous cores protruding out of the oil droplets were observed (FIG. 3A (i)-(iii)). The inner aqueous core does not merge with the continuous water phase during protrusion, indicating the existence of a shell that is protecting the inner aqueous core. Without being bound by any theory, it is believed that this shell layer comprises ionically crosslinked complexes of PAA and bPEI that form at the interface between the inner aqueous core and the middle oil phase. Eventually these snowman-shaped structures (FIG. 3A (iii)) become polyelectrolyte microcapsules upon complete separation of the inner cores from the oil droplets (FIG. 3A (iv) and FIG. 3B). The entire process takes only a few minutes from double emulsion collection. Because chloroform has higher solubility in water, the oil phase gradually becomes enriched in hexane and becomes lighter than water. Eventually, separated oil droplets float onto the top of the solution, leaving ICE microcapsules in solution, making it straightforward to collect the polyelectrolyte microcapsules as shown in FIG. 3C.

In some embodiments of ICE microcapsule generation, the chosen polyelectrolyte(s) intended for dispersal in the oil phase may not readily dissolve within the oil phase. For example, bPEI may not readily dissolve within an oil phase composed of an organic fluid that is not composed of hexane or chloroform. Other polyelectrolytes intended to be dispersed or dissolved in the oil phase may have hydrophilic properties that prevent efficient dispersal or dissolution. Thus, embodiments of ICE microcapsule generation include techniques for achieving efficient dispersal or dissolution of polyelectrolytes with hydrophilic properties in the oil phase.

Figure 4A:
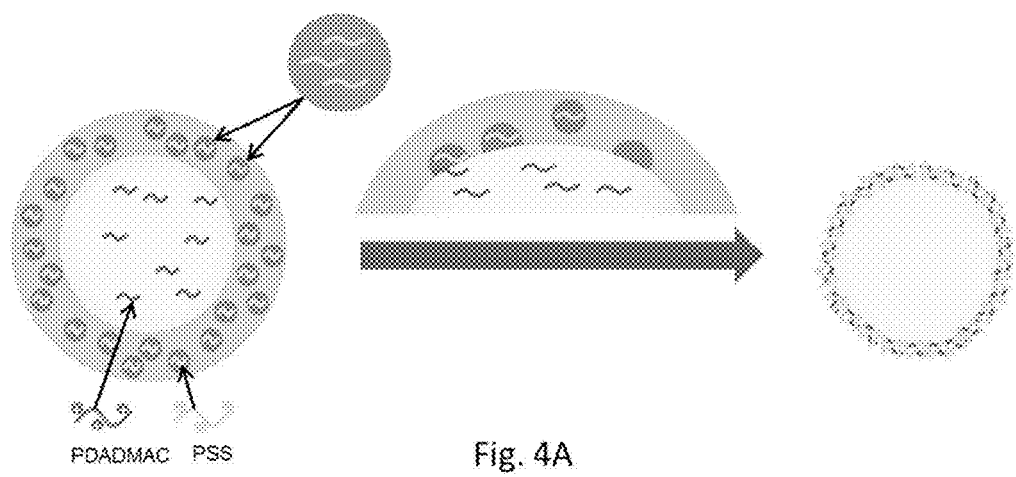
FIG. 4A provides a schematic illustration of a technique for achieving hydrophilic polyelectrolyte dispersal in the oil phase of a W/O/W double emulsion.

FIG. 4A depicts an embodiment of a technique for achieving hydrophilic polyelectrolyte dispersal in the oil phase of a W/O/W double emulsion to result in formation of a polyelectrolyte microcapsule. Hydrophilic polyelectrolyte (e.g., poly(styrene sulfonate)/"PSS") is dissolved in aqueous phase. A stabilizer such as sorbitan trioleate may be added to the aqueous phase with the hydrophilic polyelectrolyte. The aqueous phase is then dispersed in the oil phase as micro-emulsions prior to the formation of the W/O/W double emulsion. The micro-emulsions may be formed by sonication and/or homogenization. Without intending to be bound by any theory, it is hypothesized that the small aqueous droplets of the micro-emulsion within the oil phase wet the inner aqueous core of the W/O/W double emulsion, which releases the hydrophilic polyelectrolyte from the small aqueous droplets. The hydrophilic polyelectrolyte and its polyelectrolyte counterpart (e.g., poly(diallyldimethylammonium chloride)/"PDADMAC") in the inner aqueous core then complex to form the shell layer of the ICE microcapsule as depicted.

Figure 4B:
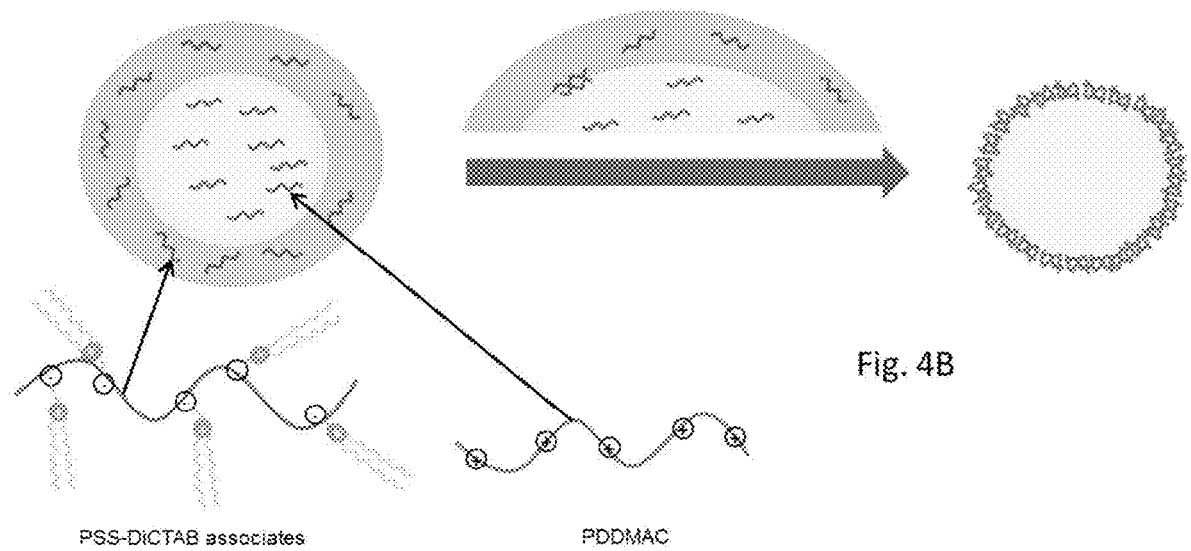
FIG. 4B provides a schematic illustration of a different technique for achieving hydrophilic polyelectrolyte dispersal in the oil phase of a W/O/W double emulsion.

FIG. 4B depicts an embodiment of another technique for achieving hydrophilic polyelectrolyte dispersal in the oil phase of a W/O/W double emulsion to result in formation of a polyelectrolyte microcapsule. Hydrophilic polyelectrolyte that is insoluble in oil phase (e.g., PSS) may be pre-modified with a surfactant (e.g., one or more "DiCTAB" compounds such as didecyldimethylammonium bromide [DiC10TAB], didodecyldimethylammonium bromide [DiC12TAB], or dihexadecyldimethylammonium bromide [DiC16TAB]) to form a complex (PSS-DiCTAB) which is soluble in the oil phase. The complex is then dissolved in the oil phase prior to forming the W/O/W double emulsion. Without intending to be bound by any theory, it is hypothesized that as the complex approaches the water/oil interface of the double emulsion, the surfactant (e.g., DiCTAB) disassociates from the hydrophilic polyelectrolyte (e.g., PSS). The hydrophilic polyelectrolyte then complexes with its counterpart polyelectrolyte (e.g., PDADMAC) from the inner aqueous core of the W/O/W double emulsion to form the shell layer of the ICE microcapsule.

Example 2 Methods

Generation of PAA Core-bPEI Shell Double Emulsions

A previously reported glass-capillary microfluidic device was used for the preparation of water-in-oil-in-water (W/O/W) double emulsions. The details have been described previously. To generate monodisperse W/O/W double emulsions, 0.1 wt % of PAA dissolved in deionized water (pH 3.7) was used as the inner phase, 0.1 wt % bPEI dissolved in a mixture of chloroform and hexane (Fisher Scientific) in a volume ratio of 1:1 containing 1-2 wt % SPAN 85 was used as the middle phase and 2 wt % poly (vinyl alcohol) solution (PVA, Sigma-Aldrich) was used as the outer phase. These three flows were introduced and controlled by using three syringe pumps. The generated double emulsions were collected in pH 2 water. To test the stability of double emulsions and observe dewetting phenomenon, the collection medium was changed to pH 3 water, pure deionized water and pH 9 water. They were prepared by adding HCl or NaOH to deionized water.

Example 3

Characterization of (PAA/bPEI) ICE Microcapsule

It was believed that the complete separation of the inner aqueous cores surrounded by polymer complex layers was induced by a dewetting phenomenon. Analogous behaviors of inner core protrusion from W/O/W double emulsions have been observed when diblock copolymers, random copolymers and phospholipids were dissolved in the middle phase of W/O/W double emulsions. These dewetting phenomena were attributed to the formation of an adhesive layer at the two W/O interfaces in double emulsions due to the changes in the solvent quality and subsequent dewetting of the oil phase on the bilayer membrane. Such protrusion eventually led to the formation of bilayer vesicles of diblock copolymers and phospholipids, although rarely has a complete separation of the inner core from the oil phase has been observed. The interfacial complexation of bPEI and PAA leads to the ionization of functional groups of the two polymers, rendering the complex layer quite oleophobic and hydrophilic. It was believed that this complex layer is highly incompatible with the oil phase and thus finds a way to minimize its contact with oil (i.e., phase separate from the oil phase).

This theory was tested by directly measuring the contact angle of a sessile drop of oil on the PAA/bPEI interfacial complex layer formed at a planar oil-water interface (FIG. 5A). It was observed that an oil drop rolls freely on the PAA/bPEI interfacial film, strongly indicating that the interfacial layer is highly oleophobic and essentially has an oil contact angle of about 180° (FIG. 5B). In contrast, in the absence of the interfacial PAA/bPEI layer, an oil drop immediately wets the interface and merges with the oil subphase (FIG. 5C). Based on these observations, it is clear that the incompatibility of the interfacial complex layer with the oil phase is a major factor that leads to the dewetting of the oil phase on the inner water-oil interface and the subsequent complete separation of the aqueous cores from the oil droplets.

It was found that the condition of the continuous phase plays an important role in maintaining the structural integrity of ICE microcapsules during inner core protrusion from double emulsions. When the continuous aqueous phase is deionized water (pH 5.5-6), it was observed that the volume of the inner droplets shrink gradually during protrusion. In contrast, when double emulsions are collected in pH 2 water, the protruded inner droplets remain stable without any shrinkage during protrusion and subsequent separation (FIG. 6). These observations strongly suggest that the polyelectrolyte complex layer is experiencing some type of tension under pH 5.5-6 and that this tension drives the capsule shrinkage. Most likely, relative magnitude of shell elasticity and membrane tension determines whether microcapsules form without any significant volume changes during dewetting.

To confirm whether all of PAA in the inner phase of the W/O/W double emulsion is consumed to form the interfacial complex layer, fluorescently labeled PAA was used to check for residual PAA in the core of ICE microcapsules. Fluorescently-labeled PAA is synthesized by conjugating aminofluorescein to about 1 mol % carboxylic acid groups of PAA (Mw: 345,000 g/mol) using the carbodiimide chemistry (a mixture of 1-ethyl-3-(3-dimthylaminopropyl)carbodiimide (EDC) and N-hydroxysuccinimide (NHS)). To track the amount of PAA left in the lumen of an ICE microcapsule, the fluorescence intensity was measured using confocal fluorescence microscopy and a line-surface plot across the capsule was observed. FIG. 7A shows that little PAA is left in the lumen and that PAA is indeed found to be located along the capsule wall. In addition, this result demonstrates that the concentration of PAA, as well as that of bPEI, can be used as processing parameters to estimate and more importantly control the shell thickness of ICE polyelectrolyte microcapsules. Assuming that all polymers in a double emulsion droplet are incorporated into the shell, the upper bound for dried shell thickness can be estimated by a simple calculation using the total amount of polymers included in the inner and middle phases of double emulsions and the size of the inner droplets; the upper limit of dry shell thickness estimated based on these assumptions is about 55 to about 75 nm (FIG. 7B). This estimation show that ICE microcapsules with nanoscale shell thickness over a wide range can be prepared by simply changing the concentration of the two polymers in the double emulsion.

Example 3 Methods

Synthesis of Fluorescently Labeled PAA

PAA (Mw: 345,000 g/mol, 200 mg) was dissolved in 20 mL of deionized water and the solution pH was adjusted to 5.0. Final molar concentration of carboxylic acid groups of the solution was 0.138 M, and 1 mol % of the carboxylic acid groups was used for this conjugation. Carboxylic acid groups of PAA were activated using 1-ethyl-3-(3-dimethylaminopropyl)carbodiimide (EDC, Sigma-Aldrich) and N-Hydroxysuccinimide (NHS, Sigma-Aldrich). 21.16 mg of EDC and 12.71 mg of NHS were added to the PAA solution in a molar ratio of 4:4:1 (EDC:NHS:AA) and they were stirred for 1 hour at room temperature. 9.59 mg of 6-aminofluorescein (Sigma-Aldrich) was added and the mixture was stirred for 12 h at room temperature. To obtain the fluorescein labeled PAA, the reacted solution was dialyzed. A dialysis cassette (Thermo Scientific, Slide-A-Lyzer Dialysis Cassettes, 10K MWCO), which can retain molecules with molecular weight higher than 10,000 g/mol, was used. Before dialysis, precipitation generated by byproducts could be removed by adjusting the solution pH to 7.0. 0.1 M NaCl solution was used as dialysis solvents. Finally, NaCl solution was changed to deionized water. The fluorescein labeled PAA solution was stored at 4° C.

Example 4

Encapsulation of Hydrophilic and Hydrophobic Agents in ICE Microcapsules

It has been surprisingly found that the use of W/O/W double emulsion templates allows ICE capsules to encapsulate both hydrophilic and hydrophobic agents simultaneously. When fluorescently labeled fluorescein isothiocyanate (FITC) dextran (molecular weight: 4,000 g/mol) was added in the inner aqueous phase and a hydrophobic dye, Nile Red, was added in the oil phase (illustrated in FIG. 8A), it was clearly observed that FITC-dextran was encapsulated in the aqueous core and Nile Red was encapsulated in the polyelectrolyte complex shell of the ICE microcapsules (FIG. 8B). Unlike previously reported fabrication methods for polyelectrolyte microcapsules, because the shell of the ICE microcapsules is formed in the presence of both oil and aqueous phases, the simultaneous encapsulation of both hydrophilic and hydrophobic species is feasible. Such a capability offers a significant advantage over conventional polyelectrolyte microcapsules for applications that require the encapsulation and release of species of opposite polarity. For example, several types of anti-cancer agents have completely different polarity and solubility, thus the delivery of multiple types of active agents using ICE microcapsules will be possible.

Example 4 Methods

Dual Incorporation of Nile Red and FITC-Dextran

To examine the dual incorporation of both FITC-dextran (Sigma-Aldrich, average molecular weight: 4,000 g/mol) and Nile Red (Sigma-Aldrich), 0.2 wt % FITC-dextran and 0.01 wt % Nile Red were added to the inner aqueous phase and middle phase solutions, respectively. 0.2 wt % FITC-dextran was used as inner contents for testing the triggered release as well. When the fluorescein-PAA was used as the inner phase, the solution was diluted three times by mixing with 0.1 wt % unlabeled PAA.

Example 5

Incorporation of Magnetic Nanoparticles into ICE Microcapsule Shells

Figure 9A:
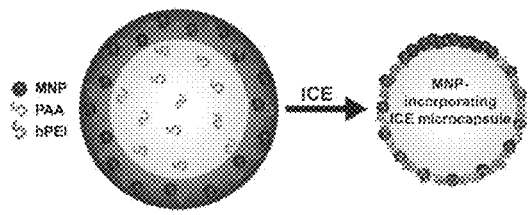
FIG. 9A provides a schematic illustration of an MNP-incorporating ICE microcapsule.
Figures 9B, 9C:
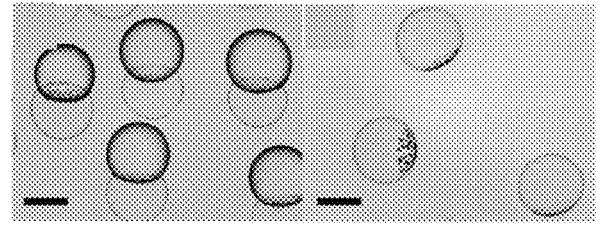
FIG. 9B shows partial dewetting of the inner aqueous core during the generation of MNP-incorporating ICE microcapsules.
FIG. 9C shows MNP-incorporating ICE microcapsules containing a high concentration of MNPs.
Figure 9D:
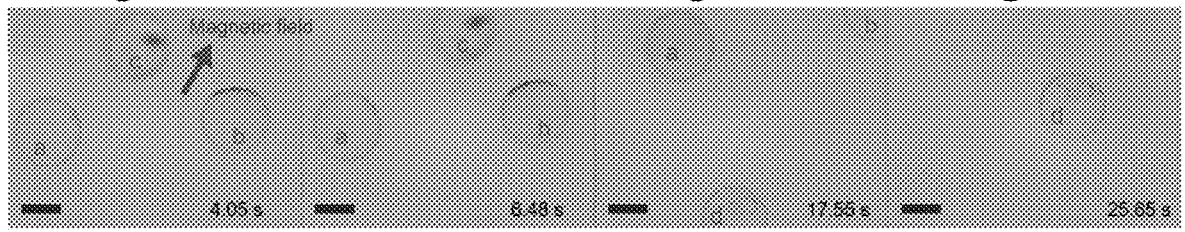
FIG. 9D provides sequential images showing movements of MNP-incorporating ICE microcapsules toward a magnetic field gradient. All scale bars for FIGS. 9A-9D=100 μm.

The utility of hydrophobic material encapsulation was further extended by incorporating hydrophobic magnetic nanoparticles (MNPs) in the ICE microcapsule shell. Such a demonstration would be extremely useful since several functional nanoparticles such as quantum dots and magnetic nanoparticles are synthesized in highly non-polar organic solvents, and such non-water soluble nanoparticles cannot be readily incorporated into polyelectrolyte microcapsules using conventional methods. Hydrophobic magnetic nanoparticles were dispersed in the oil phase of W/O/W double emulsions. FIG. 9B shows that the MNPs dispersed in the oil phase were successfully incorporated in the shell of the ICE microcapsules (see in FIG. 9A). Interestingly, in the presence of the hydrophobic nanoparticles, partial dewetting was observed. It is believed that the observed partial dewetting is due to the hydrophobization of PAA/bPEI complex layer due the presence of hydrophobic nanoparticles and potentially pinning of the contact angle during dewetting. Indeed, when the concentration of MNPs in the oil phase is increased, the three phase contact angle is decreased (FIG. 9D). MNPs are uniformly distributed in the shell of ICE microcapsules as evidenced by the coloration of ICE microcapsules. Also, a small patch of aggregated MNPs are observed in one region of ICE microcapsules after the removal of the solvent. These MNP-incorporated ICE microcapsules move in the direction of a magnetic field gradient, while pointing the patch areas toward the direction of the magnetic field gradient as shown in FIG. 9C. These results show that hydrophobic nanoparticles can be directly incorporated into the shell of ICE microcapsules without any tedious ligand exchange processes, which significantly simplifies the functionalization of polyelectrolyte microcapsules with functional nanomaterials.

Figure 9E:
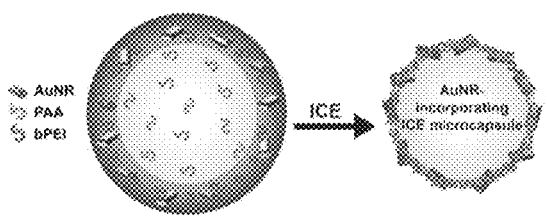
FIG. 9E provides a schematic illustration of an AuNR-incorporating ICE microcapsule; un-charged PEGylated gold nanorods (AuNR) were incorporated in the ICE microcapsule shell by dispersing AuNRs with bPEI in the oil phase.
Figures 9F, 9G:
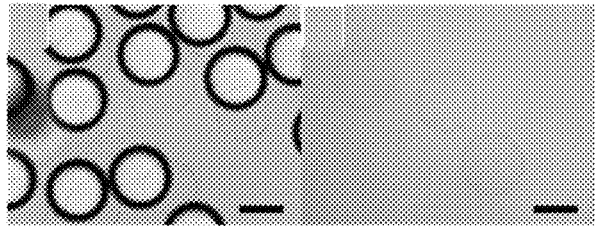
FIG. 9F shows AuNR-incorporating ICE microcapsules undergoing catastrophic rupture under NIR irradiation.
FIG. 9G shows AuNR-incorporating ICE microcapsules undergoing complete dewetting from the oil phase.
Figures 9H, 9I:
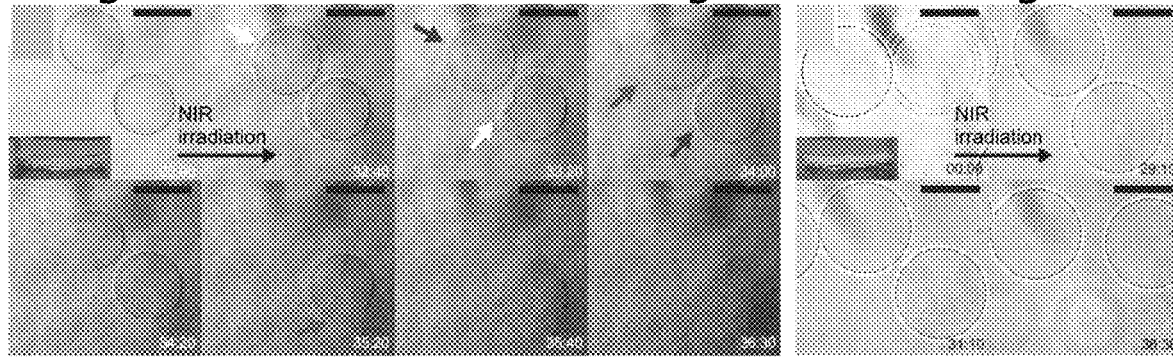
FIG. 9H shows AuNR-incorporating ICE microcapsules undergoing significant volumetric fluctuations such as shrinking and swelling before catastrophic failure occurs in one region.
FIG. 9I shows neat ICE microcapsules without AuNRs undergo neither volumetric fluctuations nor catastrophic rupture.

The functionalization of ICE microcapsules using nanoparticles was further demonstrated by incorporating a plasmonic nanomaterial and testing the light-responsive properties of ICE microcapsules. Un-charged PEGylated gold nanorods (AuNR) were incorporated in the ICE microcapsule shell by dispersing AuNRs with bPEI in the oil phase as illustrated in FIG. 9E. Interestingly, AuNR-incorporating ICE microcapsules undergo complete dewetting from the oil phase (see in FIGS. 9F and 9G). Such a phenomenon is likely due to the hydrophilic nature of PEGylated AuNRs, which renders the interfacial complex shell more hydrophilic, promoting complete separation. The incorporation of AuNRs in ICE microcapsules is evident by the appearance of violet color from the capsule suspension as shown in FIG. 9H. AuNRs are known to generate heat under near-infrared (NIR) irradiation due to their surface plasmon band and thus have been shown to induce NIR-triggered release of molecules from bulk materials, particles and capsules. NIR is an especially ideal stimulus to induce triggered release in vivo because of its ability to penetrate tissue with minimal absorption and ease of localized stimulus application. AuNR-incorporating ICE microcapsules indeed undergo catastrophic rupture under NIR irradiation as shown in FIG. 9F. These microcapsules undergo significant volumetric fluctuations such as shrinking (white arrows in FIG. 9H) and swelling (blue arrows in FIG. 9H) before catastrophic failure occurs in one region (red arrows in FIG. 9H). Under the same irradiation condition, neat ICE microcapsules without AuNRs undergo neither volumetric fluctuations nor catastrophic rupture (FIG. 9I), clearly indicating the incorporation of AuNRs led to NIR-sensitivity of ICE microcapsules.

Example 5 Methods

Generation of MNPs-ICE Microcapsule

Chloroform-dispersed magnetic nanoparticles (MNPs) were prepared. The initial product (Ferrous Inc.) was dispersed in toluene, but to use it as a component of the oil phase, the original solvent was exchanged to chloroform by evaporating the solvent and redispersing MNPs in chloroform with sonication. This process provided a clear brown solution containing well-dispersed MNPs. A mixture solution containing chloroform (50 v/v %), hexane (50 v/v %), SPAN 85 (1 wt %) and MNPs (0.05 wt %) was used to generate double emulsions. Double emulsion collection was made in a pH 2 aqueous solution. Centrifugation was used to remove residual oil droplets upon partial dewetting.

All materials for AuNR synthesis were purchased from Sigma-Aldrich. Gold nanorods (AuNRs) were synthesized by an established seed-growth method. Briefly, a solution of gold(III) chloride trihydrate, hexadecyltrimethylammonium bromide (CTAB), and sodium borohydride established Au seed nanoparticles, which were then added to a solution of gold(III) chloride trihydrate, CTAB, silver nitrate, and ascorbic acid to induce Au nanorod growth. AuNR formation was confirmed by UV-vis spectroscopy, which showed the characteristic transverse and longitudinal absorbance peaks for the gold nanorods (at approximately 515 nm and 800, respectively). The nanorods were then washed by centrifugation and resuspended in an aqueous solution of poly(ethylene glycol)-thiol (MW=5 kDa) for PEGylation. After PEGylation, the nanoparticles were centrifuged and resuspended in chloroform. The final concentration of nanorods in chloroform was determined by measuring peak absorbance of the suspension and applying the Beer-Lambert law with a molar extinction coefficient of $4.4 \times 10^9$ $M^{-1}$ $cm^{-1}$.

With the chloroform-dispersed AuNRs, an oil phase solution containing chloroform (50 v/v %), hexane (50 v/v %), SPAN 85 (1 wt %) and AuNRs (0.8 nM) was made, with which double emulsions were generated. Double emulsion collection was made in pH 2-adjusted water. After collection of ICE microcapsules, the supernatant was exchanged to pH 2-adjusted water several times to remove residual solvent. For near-infrared irradiation, a NIR laser (OEM Laser Systems) was used. The prepared ICE microcapsules with/without AuNRs were placed on a microscope stage and exposed to NIR laser with 1 W output power at 808 nm. Live imaging was performed using inverted microscope (Carl Zeiss).

Example 6

Stimuli-Responsive Properties of (PAA/bPEI) ICE Microcapsule

A hallmark of polyelectrolyte microcapsules is their stimuli-responsive properties. Because polyelectrolytes and their complexes can drastically change their conformation and interactions under changes in the pH or ionic strength, polyelectrolyte microcapsules have shown to exhibit triggered release properties. To demonstrate that ICE microcapsules indeed have such stimuli-responsiveness, the behaviors of ICE microcapsules were monitored under changes in the solution pH or ionic strength. FIGS. 10A-10C show the pH responsive characters of (PAA/bPEI) ICE microcapsules. At or below pH 5, these ICE microcapsules keep their shape without any changes (FIG. 10A). In contrast, at or above pH 7, ICE microcapsules swell significantly until they become invisible under optical microscopy (FIGS. 10B and 10C). The changes in the pH likely induce sudden changes in the interactions between the two polymers, leading to drastic swelling. Previous reports using LbL microcapsules have also shown analogous swelling behaviors of polyelectrolyte microcapsules when the pH is shifted toward the pKa of one of the polyelectrolytes.

(PAA/bPEI) ICE microcapsules show triggered release upon changes in the ionic strength of the solution at a constant pH (pH 5). As the ionic strength of the solution is increased by 100 fold from 1 mM to 100 mM, ICE microcapsules undergo sudden deformation as shown in FIG. 10D. To quantitatively monitor the release of inner contents from the ICE microcapsules caused by such deformation, the fluorescence intensity of the encapsulated FITC-dextran was measured as a function of time, as shown in FIG. 10E. The result provides clear evidence showing triggered release of FITC dextran from the ICE microcapsules by salt, again demonstrating stimuli-responsive properties of ICE polyelectrolyte microcapsules.

Example 6 Methods

Optical Imaging

For fluorescence imaging, a confocal laser scanning microscope (Olympus FluoView FV1000, Center Valley, Pa.) or a epi-fluorescence inverted microscope (Nikon Diaphot 300) was used with a CCD camera (Qimaging Retiga 2000R Fast 1394). Bright field imaging was also performed with a Nikon Diaphot 300 microscope. For colored digital imaging, an upright microscope (Carl Zeiss Axio Plan II) with a digital camera was used. All images were analyzed with Image J (NIH).

The embodiments described herein are intended to be exemplary of the invention and not limitations thereof. One skilled in the art will appreciate that modifications to the embodiments and examples of the present disclosure may be made without departing from the scope of the present disclosure.

What is claimed is:

1. A method of making polyelectrolyte microcapsules, comprising:
   with a water phase comprising a first polyelectrolyte having a charge dissolved in water, and
   an oil phase comprising a second polyelectrolyte dissolved in a hydrophobic organic fluid to produce an oil phase, the second polyelectrolyte having an opposite charge to the charge of the first polyelectrolyte,
   the first polyelectrolyte and the second polyelectrolyte being selected from polyamines having at least primary, secondary, tertiary, or quaternary amines, from polybases, and from polyacids,
   injecting the water phase, the oil phase, and an outer water phase comprising water into a capillary microfluidic device under such conditions that the injecting gives rise to a water-in-oil-in-water (W/O/W) double emulsion,
   the W/O/W double emulsion comprising the water phase as an inner phase, the oil phase as a middle phase, and the outer water phase as an outer phase,
   the first and second polyelectrolytes forming polyelectrolyte microcapsules comprising a shell that comprises a polyelectrolyte complex formed of the first and second polyelectrolytes present at interfaces between the inner water phase and the middle oil phase, and
   the polyelectrolyte microcapsules being formed following a spontaneous dewetting process whereby the polyelectrolyte microcapsules separate from the middle oil phase.

2. The method of claim 1, further comprising dissolving the first polyelectrolyte in the water phase and dissolving the second polyelectrolyte in the oil phase prior to forming the W/O/W double emulsion.

3. The method of claim 1, further comprising adding one or more additives to the water phase and adding one or more additives to the oil phase prior to forming the W/O/W double emulsion, wherein the additives are selected from the group consisting of stabilizing agents, surfactants, pH adjusters and combinations thereof.

4. The method of claim 1, further comprising adding at least one active ingredient to the inner water phase prior to forming the W/O/W double emulsion.

5. The method of claim 4, wherein the at least one active ingredient is selected from the group consisting of active pharmaceutical ingredients, herbicides, pesticides, plant nutrients, antioxidants, anti-bacterial agents, fragrances, edible actives, flavorants, vitamins, minerals, and combinations thereof.

6. The method of claim 1, further comprising adding one or more hydrophobic materials to the oil phase prior to forming the W/O/W double emulsion.

7. The method of claim 6, wherein the one or more hydrophobic materials comprise one or more nanoparticles.

8. The method of claim 1, further comprising: forming a complex between a surfactant and the second polyelectrolyte to form a surfactant-modified polyelectrolyte prior to forming the W/O/W double emulsion; and
   dissolving the surfactant-modified polyelectrolyte in the oil phase prior to forming the W/O/W double emulsion.

9. The method of claim 1, further comprising:
   dissolving the second polyelectrolyte in an aqueous phase prior to forming the W/O/W double emulsion; and
   forming micro-emulsions of the aqueous phase comprising the dissolved second polyelectrolyte within the oil phase prior to forming the W/O/W double emulsion.

10. A pharmaceutical composition comprising a pharmaceutical carrier and a plurality of polyelectrolyte microcapsules in accordance with claim 8, wherein the polyelectrolyte microcapsules comprise one or more active pharmaceutical ingredients.

11. An agricultural composition comprising an agricultural carrier and a plurality of polyelectrolyte microcapsules in accordance with claim 8, wherein the polyelectrolyte microcapsules comprise one or more herbicides, pesticides, and/or plant nutrients.

12. A cosmetic composition comprising a cosmetic carrier and a plurality of polyelectrolyte microcapsules in accordance with claim 8, wherein the polyelectrolyte microcapsules comprise one or more antioxidants, anti-bacterial agents, and/or fragrances.

13. A food product comprising one or more food ingredients and a plurality of polyelectrolyte microcapsules in accordance with claim 8, wherein the polyelectrolyte microcapsules comprise one or more foodstuffs, flavorants, nutrients, vitamins, and/or minerals.

14. The method of claim 6, wherein the hydrophobic materials are incorporated into the polyelectrolyte complex.

15. The method of claim 6, wherein the one or more hydrophobic materials comprise dyes, drugs, and/or conjugated polymers.

16. The method of claim 7, wherein the one or more nanoparticles include $SiO_2$, $TiO_2$, $Fe_2O_3$, $Al_2O_3$, gold, and silver.

* * * * *